(12) United States Patent
Bonte et al.

(10) Patent No.: US 7,678,380 B2
(45) Date of Patent: *Mar. 16, 2010

(54) COSMETIC TREATMENT METHOD FOR FIGHTING AGAINST SKIN AGEING EFFECTS

(75) Inventors: Frédéric Bonte, Orleans (FR); Marc Dumas, Orleans (FR); Catherine Heusele, Limours (FR); Jacques Le Blay, Leves (FR)

(73) Assignee: LVMH Recherche, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/244,741

(22) Filed: Sep. 17, 2002

(65) Prior Publication Data

US 2003/0059484 A1 Mar. 27, 2003

Related U.S. Application Data

(63) Continuation of application No. 09/701,341, filed as application No. PCT/FR99/01261 on May 28, 1999, now Pat. No. 6,471,972, which is a continuation-in-part of application No. 09/297,679, filed as application No. PCT/FR97/01988 on Nov. 6, 1997, now Pat. No. 6,193,975.

(30) Foreign Application Priority Data

Nov. 7, 1996 (FR) .................................. 96 13585
May 29, 1998 (FR) .................................. 98 06822

(51) Int. Cl.
*A61K 8/36* (2006.01)
(52) U.S. Cl. .................... 424/401; 424/725; 424/773; 514/561
(58) Field of Classification Search ............... 424/401, 424/642, 59, 62, 70.1, 70.9, 74, 725, 773, 424/681, 682; 514/847, 561; 530/379
See application file for complete search history.

(56) References Cited

U.S. PATENT DOCUMENTS 3,274,063 A * 9/1966 Escherich et. al. .......... 514/561
4,405,596 A * 9/1983 Helbig et al. ............... 424/478
4,524,067 A * 6/1985 Arichi et al. ............... 514/33
4,837,012 A * 6/1989 Kiffel et al. ............... 424/70.8
4,938,969 A 7/1990 Schinitsky et al. .......... 424/642
5,256,649 A * 10/1993 Le Fur et al. .................. 514/46
5,679,359 A * 10/1997 Diezel ........................ 424/401
5,723,149 A * 3/1998 Bonte et al. ................. 424/450
5,738,879 A * 4/1998 Rine .......................... 424/708
5,804,168 A 9/1998 Murad ........................ 424/59
6,495,147 B1 * 12/2002 Dumas et al. ............... 424/401
2002/0098213 A1 * 7/2002 Bonte et al.

FOREIGN PATENT DOCUMENTS

| FR | 2 406 438 | 5/1979 |
| FR | 2 669 225 | 5/1992 |
| FR | 2 704 390 | 11/1994 |
| FR | 2 713 483 | 6/1995 |
| FR | 96/25143 | 8/1996 |
| FR | 2 735 981 | 1/1997 |
| SU | 1033138 A | 8/1983 |
| WO | 94/22421 | 10/1994 |
| WO | 97/09963 | 3/1997 |
| WO | 98/19664 | 5/1998 |

OTHER PUBLICATIONS

International Cosmetic Ingredient Dictionary and Handbook, Seventh Edition, vol. 1, 1997, pp. 767-768.*
Derwent Abstracted-Pub No. EP 558509B, Mar. 15, 1995, Bonte et al., Compositions for the hair and scalp preventing hair loss.

* cited by examiner

*Primary Examiner*—Ardin Marschel
*Assistant Examiner*—James D Anderson
(74) *Attorney, Agent, or Firm*—The Nath Law Group

(57) ABSTRACT

The present invention relates to a method of cosmetic treatment for combating the effects of skin ageing and to novel cosmetic compositions which are particularly suitable for carrying it out. According to the invention, at least one agent for promoting the adhesion of the keratinocytes of the epidermal basal layer to the dermo-epidermal junction, especially to the collagen IV of said junction, such as, in particular, a divalent metal salt or complex, preferably magnesium aspartate or magnesium chloride, is used, optionally in association with a stimulant of collagen IV synthesis and/or a stimulant of collagen VII synthesis.

11 Claims, No Drawings

US 7,678,380 B2

COSMETIC TREATMENT METHOD FOR FIGHTING AGAINST SKIN AGEING EFFECTS

This application is a Continuation Application of U.S. patent application Ser. No. 09/701,341, filed Nov. 28, 2000, now U.S. Pat. No. 6,471,972, which is a U.S. 371 national phase filing of International Patent Application PCT/FR99/01261 with an International Filing date of May 28, 1999, which is a Continuation-In-Part (CIP) of U.S. patent application Ser. No. 09/297,679, filed May 6, 1999, now U.S. Pat. No. 6,193,975, Feb. 27, 2001, which is a U.S. 371 national phase filing of International Patent Application PCT/FR97/01988 with an International Filing date of Nov. 6, 1997.

The present invention relates to a method of cosmetic treatment for combating the effects of skin ageing and to novel cosmetic compositions which are particularly suitable for carrying it out.

The dermo-epidermal junction (DEJ) is known to be a complex structure assuring the cohesion and exchanges between the dermis and epidermis which are essential for the skin to function properly.

It has been discovered that it is possible to slow down or treat skin ageing, and in particular to reduce the depth of wrinkles, and/or slow down their appearance, and/or restore the tonicity and elasticity of the skin, and/or slow down the decrease in tonicity and elasticity of the skin, by means of a method of cosmetic treatment corresponding to a novel concept which consists in using a cosmetically acceptable agent to promote the adhesion of the keratinocytes of the epidermal basal layer to the dermo-epidermal junction, especially to the type IV collagen, also called collagen IV, which is a major constituent of said dermo-epidermal junction. It is this discovery which constitutes the basis of the present invention.

Thus, according to its most general feature, the present patent application aims to cover a method of cosmetic treatment for slowing down or treating skin ageing, and in particular for reducing the depth of wrinkles, and/or slowing down their appearance, and/or restoring the tonicity and elasticity of the skin, and/or slowing down the decrease in tonicity and elasticity of the skin, characterized in that an amount of at least one agent for promoting the adhesion of the keratinocytes of the epidermal basal layer to the dermo-epidermal junction, especially to the collagen IV of said junction, is applied to the skin.

It has furthermore been shown that particularly remarkable results are obtained within the framework of the present invention if the above-mentioned adhesion promoter is applied in association with an effective amount of at least one stimulant of collagen IV synthesis and/or with an effective amount of at least one stimulant of collagen VII synthesis.

The expression "stimulant of collagen IV or collagen VII synthesis" is understood within the framework of the present description as meaning any agent which is capable of producing or maintaining a high level of collagen IV in the dermo-epidermal junction, either by increasing the biosynthesis or by inhibiting the enzymes which degrade the constituent proteins of this product.

In one advantageous embodiment of the invention, the above-mentioned adhesion promoter is a divalent metal salt or complex, particularly a magnesium or zinc salt or complex, or a mixture of divalent metal salts or complexes.

The divalent metal salt or complex is preferably a divalent metal chloride or a divalent metal salt or complex with a cosmetically acceptable organic acid such as an amino acid, for example aspartic acid, asparagine, proline, glutamic acid, methionine, leucine, histidine or lysine, or a $C_2$-$C_{12}$ aliphatic alpha-hydroxy acid, particularly citric acid, glycolic acid, gluconic acid, malic acid, lactic acid or 2-hydroxybutyric acid.

In one currently preferred embodiment of the invention, said divalent metal salt or complex is magnesium aspartate or magnesium chloride.

According to one particular characteristic of the method of the present invention, the above-mentioned adhesion promoter is applied in the form of a composition in which it is present in an amount of between 0.0001 and 5% by weight, preferably of between 0.001 and 1% by weight, based on the total weight of the composition.

Any stimulant of collagen IV synthesis can be used within the framework of the method according to the present invention.

In one currently preferred embodiment, the stimulant of collagen IV synthesis is selected from soya saponins and soya sapogenols, preferably of type A and type B, and plant extracts rich in such compounds, preferably extracts of soya (*Glycine max*) or alfalfa (*Medicago sativa*).

In another preferred embodiment, the stimulant of collagen IV synthesis is a whole range of saponins from roots of *Medicago sativa*.

Likewise, any stimulant of collagen VII synthesis can be used within the framework of the present invention.

In one currently preferred embodiment, the stimulant of collagen VII synthesis is an extract of *Potentilla erecta*.

In another preferred embodiment, the stimulant of collagen VII synthesis is an extract of *Bertholletia*, particularly *Bertholletia excelsa*.

According to a second feature, the present patent application aims to cover novel cosmetic compositions which are particularly suitable for carrying out the method described above.

These compositions are essentially characterized in that they contain an effective amount of at least one agent for promoting the adhesion of the keratinocytes of the epidermal basal layer to the dermo-epidermal junction, especially to the collagen IV of said junction, said agent being selected from magnesium or zinc salts or complexes, in association with an effective amount of at least one stimulant of collagen IV synthesis and/or an effective amount of at least one stimulant of collagen VII synthesis.

In these compositions, the various adhesion promoters and stimulants of collagen IV synthesis or collagen VII synthesis are as described above within the framework of the general description of the method according to the invention.

The compositions of the invention may also advantageously comprise at least one substance for promoting the synthesis of the constituents of the extracellular matrix of the skin.

Furthermore, the compositions according to the invention can also contain at least one substance selected from the group consisting of vitamins, particularly the vitamins of group A (retinol) and group C and derivatives thereof such as the esters, especially the palmitates and propionates, tocopherols, xanthines, particularly caffeine or theophylline, retinoids, particularly vitamin A acid, extracts of *Centella asiatica*, asiatic and madecassic acids and glycosylated derivatives thereof such as asiaticoside or madecassoside, extracts of *Siegesbeckia orientalis*, extracts of *Commiphora mukul* and extracts of *Eriobotrya japonica*, cosmetically acceptable silicon derivatives such as polysiloxanes, silanols and silicones, $C_3$-$C_{12}$ aliphatic alpha-keto acids, particularly pyruvic acid, $C_2$-$C_{12}$ aliphatic alpha-hydroxy acids, particularly citric acid, glycolic acid, malic acid and lactic acid, amino acids, particularly arginine, citrulline and threonine, ceramides, glycoceramides, sphingosine derivatives, particularly type II and III ceramides, phospholipids, forskolin and derivatives thereof, extracts of Coleus, extracts of *Tephrosia*, elastase inhibitors, particularly ellagic acid and soya peptides, collagenase inhibitors, particularly plant peptides and extracts such as extracts of roots of *Coptidis* and extracts of roots of *Scutellaria baicalensis Georgi*, flavonoids such as wogonin, baicalin and baicalein, aqueous-ethanolic extracts of leaves of *Ginkgo biloba, Mosla chinensis, Salvia officinalis* and *Cinnamomum cassia*, catechuic extracts of *Camellia sinensis* and aqueous extracts of bean shells of *Theobroma cacao*, anti-inflammatories, particularly phospholipase A2 inhibitors, soothing agents, particularly extracts of liquorice, glycyrrhetinic acid and ammonium glycyrrhizinate, hydrating agents, particularly polyols, propylene glycol, butylene glycol, glycerol and hyaluronic acid, agents for combating stretch marks, particularly extracts of horse chestnut and escin, agents for protecting or improving the microcirculation, particularly bioflavonoids from *Ginkgo biloba*, isodon, extracts of *Ami visnaga*, visnadine and ruscogenin, free radical inhibitors, particularly polyphenols such as PCO (procyanidolic oligomers) and derivatives thereof and plant extracts, particularly extracts of *Curcuma longa*, antiseborrhea agents, such as a 5-alpha-reductase inhibitor, particularly an extract of *Pygeum africanum*, and stimulants of the microcirculation of the blood, such as cepharanthine and methyl nicotinate.

The compositions according to the invention can advantageously contain substances for protecting the skin from the harmful effects of the sun, such as solar filters, individually or in combination, especially UV A filters and UV B filters, particularly titanium oxides and zinc oxides, oxybenzone, Parsol MCX, Parsol 1789 and filters of vegetable origin, substances for limiting the damage caused to the DNA, particularly those for limiting the formation of thymine dimers, such as ascorbic acid and derivatives thereof and/or Photonyl®, and substances for contributing to the elimination of liver spots, such as inhibitors of melanin or tyrosinase synthesis.

Other objects, characteristics and advantages of the invention will become clearly apparent to those skilled in the art from the following explanatory description referring to several Examples relating to tests performed, and Examples of cosmetic formulations, which are given simply by way of illustration and cannot therefore in any way limit the scope of the invention.

All the percentages are given by weight in the Examples, unless indicated otherwise.

EXAMPLE 1

Test for the Adhesion of Normal Human Keratinocytes to Type IV Collagen with the Aid of an Agent According to the Invention for Promoting the Adhesion of the Keratinocytes to the Dermo-Epidermal Junction, Consisting of Magnesium Chloride or Aspartate in this Test.

The object of the present test is to demonstrate the efficacy of an agent according to the invention for promoting the adhesion of the keratinocytes to the dermo-epidermal junction, said agent preferably consisting of magnesium chloride or aspartate.

Within this framework, said test is carried out in the following manner:

1. Coating of the Adhesion Surfaces with Type IV Collagen

Wells of microplates (Falcon) are covered with 6 $\mu$g/cm$^2$ of sterile type IV human collagen (from Sigma).

Each well is then incubated overnight at +4° C. with a 4 mg/ml solution of bovine albumin, BSA, from Sigma.

The wells are then rinsed twice with a phosphate buffer, PBS (phosphate buffered saline), from Gibco.

2. Preparation of the Cultures of Normal Human Keratinocytes

The epidermal cells are obtained from healthy surgical skin originating from the mammary region of a 53-year-old female caucasian donor.

The skin fragments are incubated in 0.25% w/v trypsin for 18 hours at +4° C. to separate the dermis and epidermis and to obtain, by agitation, a suspension of epidermal cells. The trypsin is neutralized with fetal calf serum, FCS, from Gibco.

The cells are inoculated into flasks defining a surface area of 75 cm$^2$ and are cultured in keratinocyte proliferation medium, K-SFM, from Gibco, to the point of confluence, when they are subcultured.

The cells used for the experiments for adhesion to the collagen substrate were not subcultured beyond the first subculture (called P0 or P1).

3. Treatment of the Keratinocytes with the Product of the Invention, Consisting of Either Magnesium Chloride or Magnesium Aspartate Tryspin (trypsin containing 0.1%-0.02% w/v of EDTA, from Gibco) is added to the keratinocyte cultures, and the cell suspension is placed in E 199 medium from Gibco, complemented with 2 mM L-glutamine and 4 mg/ml of BSA and containing, according to the invention, 0.25, 0.5 or 1 mM magnesium chloride or 0.25 mM magnesium aspartate.

The keratinocytes are then incubated for 30 minutes at +4° C. before the step for adhesion to the substrate coated with collagen IV is carried out.

4. Measurement of the Adhesion of the Keratinocytes to the Type IV Collagen

The keratinocytes are inoculated into each well at a density of 93,000 cells/cm$^2$ in E 199 medium from Gibco, containing 2 mM L-glutamine from Gibco and 4 mg/ml of BSA (bovine serum albumin). After incubation for one hour at +4° C., the wells are rinsed with PBS, the adhering cells are then lyzed with 0.1 N sodium hydroxide solution and the cellular proteins are then quantified by means of the calorimetric method and bicinchoninic acid (BCA from Sigma).

A calibration is performed in parallel with BSA solubilized in 0.1 N sodium hydroxide solution, enabling the optical density (OD) values to be converted to micrograms ($\mu$g) of proteins per well.

5. Statistical Analysis

The adhesion A is expressed in micrograms of cellular proteins per culture well and the values shown in Table I correspond to a mean value obtained from 6 wells per product concentration, the products being the untreated cells, the cells treated with a magnesium chloride or aspartate concentration of 0.25 mM, the cells treated with a magnesium chloride concentration of 0.5 mM and the cells treated with a magnesium chloride concentration of 1 mM.

These adhesion values between treated and untreated cells were compared by the 0.7 Student t-test at the p=0.05 threshold in order to assess their level of significance.

The results obtained from the experiment on the keratinocytes of a 53-year-old donor are listed in Table I below:

TABLE I

|  | A | Standard deviation | Student t-test |
|---|---|---|---|
| Control | 3.52 | 0.9 |  |
| Magnesium chloride (0.25 mM) | 4.32 | 0.7 | Not significant (p = 0.12) |

TABLE I-continued

| | A | Standard deviation | Student t-test |
|---|---|---|---|
| Magnesium chloride (0.5 mM) | 4.54 | 1.1 | Not significant (p = 0.1) |
| Magnesium chloride (1 mM) | 4.57 | 0.75 | Significant (p = 0.05) |
| Magnesium aspartate (0.25 mM) | 5.39 | 0.8 | Significant (p = 0.004) |

A = adhesion in µg of protein per well (mean)

The results listed in Table I above show that, compared with the control cultures, there is an increase in the adhesion of the keratinocytes to the type IV collagen in the presence of magnesium chloride as from the 0.25 mM concentration, but this is only statistically significant as from 1 mM.

The percentage increase in adhesion obtained with magnesium chloride at the 1 mM concentration is +31.

As far as magnesium aspartate is concerned, this also promotes the adhesion of the keratinocytes, but more strongly than magnesium chloride. In fact, the increase in adhesion is highly significant as from the 0.25 mM concentration.

The percentage increase in adhesion obtained with magnesium aspartate at the 0.25 mM concentration is +54.

Under these conditions, it is thus seen that these magnesium salts, and more especially magnesium aspartate, are of particular value because they produce highly significant results at low doses, enabling them to be used at low concentrations and hence with a good degree of safety.

EXAMPLE 2 OF THE INVENTION

1. Composition of an Anti-Wrinkle Cream

| | |
|---|---|
| Magnesium L-aspartate | 0.3 g |
| Dry extract of *Potentilla erecta* | 0.01 g |
| Hyaluronic acid (sodium salt) | 0.06 g |
| Glycerol | 5.15 g |
| Total dry extract of *Centella asiatica* | 0.1 g |
| Vitamin A palmitate solution (1 million IU/g) | 0.1 g |
| Vitamin E acetate | 0.5 g |
| Dry extract of Perilla | 0.5 g |
| O/W emulsion excipient plus perfume and preservatives | qsp 100 g |

2. Testing of this Cosmetic Composition for Evaluation of its Anti-Wrinkle Efficacy A—Principle To evaluate the anti-wrinkle efficacy of this cosmetic product on "crow's feet", negative replicas of skin are made at time 0 and then after 28 days of twice daily application of the above composition in the form of a cream.

These replicas, illuminated by a glancing light casting shadows behind each wrinkle, are analyzed with the aid of a commercially available image-analyzing software, called "Quantirides", developed by MONADERM (Monaco).

B—Equipment

B.1—For Taking Impressions

Adhesive rings from 3M, of internal diameter 24 mm and external diameter 40 mm, are used.

The product Silflo® from FLEXICO UK, based on a silicone polymer combined with a catalyst, is used to take impressions.

B.2—For Analyzing the Impressions

The following are used:

a COHU 4910—RS 170 and CCIR Monochrome CCD camera, which is a high-definition and very low-noise camera equipped with a fixed-focus lens and an $18 \times 10^8$ mm F 2.5 manual zoom lens;

a real-time high-resolution image acquisition card;

a Monaspot glancing illumination lamp with an angle of incidence of 35°;

a Kaiser RS 1 tripod, a 450×500 mm anti-reflection matte black plate and a 1000 mm height-adjustable column graduated in centimeters, equipped with an RA1 projection arm;

a special support for positioning and orientating the replicas; the above-mentioned Quantirides software; and a microcomputer and a printer.

C—Protocol

1. Volunteers 30 subjects aged between 34 and 59 years, comprising 29 women and 1 man, were selected.

2. Test Product

The test product is the composition in the form of a cream described above in section 1.

3. Application

The cosmetic composition is applied twice a day, in the morning and evening, to the whole of one temporal zone of the face (crow's foot) for 28 days. The amount applied can be estimated at about 1.5 to 2 mg per $cm^2$, depending on what the subject is accustomed to. The other, "untreated" temporal zone serves as the control.

For three days preceding the start of the test, and throughout the entire test, no other cosmetic product is used on the treated zone or the control zone.

4. Experimental Conditions

Temperature: from 20 to 22° C.

Relative humidity: from 40 to 50%

An impression of the control and treated zones is made at time 0 and after 28 days of treatment. An adhesive ring is positioned over the study zone. A thin layer of Silflo®, mixed with a few drops of catalyst (3 drops per 3 g of Silflo®) immediately before use, is applied to the inside of the zone delimited by the ring. The paste must be spread carefully to avoid the formation of air bubbles. After polymerization of the paste, a drying time of 4 minutes 30 seconds, the ring is detached from the skin, bringing the replica with it. At the end of the study, these impressions are analyzed with the aid of the Quantirides software.

D. Parameters Studied

For each subject and for each side of the face, on D0 (the day before the first application) and D28 (day 28 of application) processing of the impressions by the image analyzer made it possible to calculate the following parameters representing the state of wrinkling of the skin:

a) the total surface area of the wrinkles in $mm^2$;

b) the number of wrinkles;

c) the total length of the wrinkles in mm;

d) the mean length in mm; and e) the mean depth in µm.

E. Processing of the Results: Change in the Treated Side and the Control Side

1. Calculation

Mean Variation of the Parameters

The following is calculated for each site and each parameter:

$$\text{Variation.}(\%) = \left(\frac{m(t) - m(0)}{m(0)}\right) \times 100$$

where: m(t)=mean value of the parameter studied at time t m(0)=mean value of the parameter studied at time 0

2. Statistical Significance
Wilcoxon Test

The non-parametric Wilcoxon test is used, which makes it possible to take account of the small number of subjects and is applicable to the in vivo study of biological parameters in humans.

A comparison of the paired series is made as follows: the difference is evaluated for each pair and the differences are then placed in increasing order of absolute value; it is also indicated for each one whether it is positive or negative, zero differences being eliminated.

The quantities to be considered are as follows:
M=sum of the ranks of negative difference
P=sum of the ranks of positive difference
T=the smaller of the two totals, M or P The significance limit accepted for n<10 persons is below 10%.

The significance limit accepted for n≧10 persons is below 5%.

The Wilcoxon test was applied to the difference (m(t)−m(0)) at the different times at the two sites in order to compare the change in the treated site with the change at the control site.

A Wilcoxon test was applied to the raw values at time 0 (m(0)) in order to compare the change in each site with time.

3. Results

The results obtained from the experiment are listed in Table II below.

The control and treated sites are comparable at time 0.

The values shown in column 4 under the heading "total variation" correspond to the difference between the variation in the treated subjects and the variation in the control subjects.

TABLE II

| | Variation in control subjects % | Variation in treated subjects % | Total variation % | Statistics (Wilcoxon) |
|---|---|---|---|---|
| Total surface area of wrinkles (mm$^2$) | 6.6 | −19.7 | −26.3 | Significant (p = 0.015) |
| Number of wrinkles | 16.5 | −14.3 | −30.8 | Significant (p = 0.004) |
| Total length (mm) | 12.9 | −16.7 | −29.6 | Significant (p = 0.0014) |
| Mean length (mm) | −2.6 | −1.7 | 0.9 | Not significant |
| Mean depth (μm) | 0.3 | −2.0 | −2.3 | Not significant |

E. Conclusion

After twice daily application of the composition according to the invention for 28 days, the change in the treated crow's foot is compared with the change in the control crow's foot to reveal a significant decrease in the large and small wrinkles and a slowing-down of their formation: the total surface area of the wrinkles drops by 26%, their number by 31% and their total length by 30%.

Example 3 of the invention: W/O anti-wrinkle night cream

| | |
|---|---|
| Magnesium aspartate | 0.3 g |
| Dry extract of *Potentilla erecta* | 1 g |
| Glycerol | 5 g |
| Propylene glycol | 2 g |
| Ceramide III | 0.04 g |
| UV filters | 9 g |
| Methylsilanol mannuronate | 0.05 g |
| Dry extract of *Perilla frutescens* | 1 g |
| Dry extract of *Centella asiatica* | 0.5 g |
| Soya peptide | 1 g |
| Retinol palmitate | 0.2 g |
| W/O emulsion excipient | qsp 100 g |

Example 4 of the invention: firming cream for slowing down and combating the appearance of wrinkles

| | |
|---|---|
| Magnesium aspartate | 0.2 g |
| Glycerol | 5 g |
| Propylene glycol | 2 g |
| Ceramide II | 0.04 g |
| Parsol MCX | 5 g |
| Oxybenzone | 3 g |
| Methylsilanol mannuronate | 0.05 g |
| Madecassoside | 0.5 g |
| Retinol | 4000 IU |
| Saponins from Medicago sativa | 0.02 g |
| Retinol palmitate | 0.04 g |
| O/W emulsion excipient | qsp 100 g |

Example 5 of the invention: anti-wrinkle tightening gel

| | |
|---|---|
| Zinc gluconate | 0.3 g |
| Dry extract of *Bertholletia excelsa* | 0.3 g |
| Soya saponin | 0.05 g |
| Retinol palmitate | 0.06 g |
| Alpha-tocopherol acetate | 0.1 g |
| Lactic acid | 1.5 g |
| Glycolic acid | 0.2 g |
| Ethanol | 5 g |
| Gel excipient | qsp 100 g |

Extracts of *Potentilla erecta*

It will be possible for various solvents to be used for obtaining an extract of the plant used in accordance with the present invention. However, water, a $C_1$ to $C_4$ alcohol, a $C_2$ to $C_6$ glycol, or any mixture of the solvents mentioned above will advantageously be selected, in particular an aqueous alcohol mixture or aqueous glycol mixture. Of course, the extraction solvent is selected such that it be liquid at ordinary temperature, i.e. 20-25° C.

Water will be the extraction solvent which is preferably used according to the invention.

It is more particularly preferred to use methanol or ethanol from the alcohols mentioned above. It is preferred to use ethylene glycol, propylene glycol or butylene glycol from the glycols. Butylene glycol will advantageously be selected.

The extract of the plant Potentilla erecta will advantageously be obtained from the rhizome of this plant in the two fields of cosmetic and pharmaceutical applications.

Thus, according to a particularly advantageous variant, an aqueous extract of the rhizome of Potentilla erecta will be used for the preparation of the compositions of the invention.

The cosmetic or pharmaceutical compositions, notably dermatological compositions of the invention, will advantageously contain 0.0001% to 5%, preferably between 0.01 and 0.5% by weight of said extract of Potentilla erecta with respect to the total weight of the composition.

In one currently preferred embodiment, the stimulant of collagen VII synthesis is an extract of Potentilla erects.

EXAMPLE 6

Preparation of a Methanol Extract of Rhizomes of Potentilla erecta

One part by weight of the plant rhizomes is extracted thrice in a row with 10 parts of methanol, under reflux, each time for 30 minutes. All the extracts are combined after filtration.

The extract is then concentrated up to the total removal of the solvent. A product is thus recovered in the form of a dry extract.

EXAMPLE 7

Preparation of an Extract of Rhizomes of Potentilla Erecta by Aqueous Extraction 50 g of the plant rhizomes, finely ground, are used, and an extraction is made with 500 ml of boiling water for 30 minutes. After filtering on a grid of porosity 0.45 μm, the solid residue is extracted twice in a row under the same conditions as the first extraction, with 500 ml of water. All the aqueous extracts were then combined and then lyophilised. A dry extract is thus obtained in the form of a powder.

EXAMPLE 8

Demonstration of the Stimulation of the Synthesis of Collagen VII by an Aqueous Extract of Rhizomes of Potentilla erecta The above test was carried out on the aqueous extract in the form of a lyophilised powder, hereinafter referred to as AE, obtained according to the method described in Example 7.

The tests were carried out blind.

1-Protocol of the Test a) Source of the Keratinocytes

Cultures of normal human keratinocytes (NHK) are established from a surgical sample of healthy skin. In the present study, the tests are carried out on a cell strain originating from a lifting of a 58-year old Caucasian woman.

b) Culture Conditions:

The keratinocytes are kept in a complete SFM (Serum Free Medium) (designated as SFMc, GIBCO). The cells were under cultivated once from the first culture (i.e. one passage, designated P1).

c) Treatment Conditions:

The sowing of the cells is carried out in a 96-well culture plate at the rate of 30,000 NHK per well in SFMc. After 24 hours of incubation necessary for a good adherence of the cells, the medium is replaced by an SFMc diluted to 2%, limiting the proliferation of the keratinocytes. The mother solutions of product obtained according to Example 7 (referred to as AE in Table III) are prepared extemporaneously in DMSO at concentrations of 1-2.5-5 mg/ml and introduced into the study medium at 0.1% V/V final (i.e. the concentrations tested: 1-2.5-5 μg/ml). The control received the excipient of the product, i.e. 0.1% V/V of DMSO. Six cultures were prepared for each of the three concentrations and for the control test. The viability test XTT, as well as the microscopic observation of the cells, did not reveal any cytotoxic effects of the product at concentrations lower than 10 μg/ml. (XTT kit, BOEHRINGER, Ref. 1465015).

The cells are placed in contact with the treatment medium for 72 hours, the time required for an optimal synthesis of collagen VII according to a prior kinetic study.

The incubation supernatants are taken with a view to determining the collagen VII secreted. A determination of the proteins is carried out on the cell mat which remains in the wells (BCA method, SIGMA), with the aim of establishing a relationship between the amounts of collagen VII secreted and the levels of cell proteins.

d) ELISA Determination of the Collagen VII:

The collagen VII determination protocol by an ELISA method was adapted from that used for determination of collagen I (M. DUMAS, C. CHAUDAGNE, F. BONTE, A. MEYBECK: "In vitro biosynthesis of type I and III collagens by human dermal fibroblasts from donors of increasing age", Mechanisms of Ageing and Development, 73 (1994) 179-187).

The following modifications were made:

$1^{st}$ antibody: Human Type VII monoclonal mouse anti-collagen antibody, isotype IgG1 (Life Technologies, Ref. 12073-011, Lot FB2b01).

$2^{nd}$ antibody: Mouse total anti-IgG goat antibodies, coupled to alkaline phosphatase (Interchim, Ref. 115-056-062, Lot 26793).

e) Expression of the Results and Statistical Interpretation:

In the absence of commercially available human type VII collagen for establishing a standard range, the results of the secretion of collagen VII by the keratinocytes are expressed in units of optical density, to which the determination control test is subtracted (designated O.D.—Blank). These values are brought back to the levels of cell proteins of the corresponding well (for 72 hours of incubation).

The activity of the product is evaluated by the percentage of stimulation:

The results obtained on the treated cultures (n=6) and control cultures (n=6) are compared by the non-paired Student test, the significance threshold retained being $p<0.05$.

The activity of product A on the collagen VII was the subject of a confirmation on the same NHK strain.

Results—Conclusion

The results are given in Table III below, from the average of the measurements on the various cultures:

TABLE III

| COLLAGEN VII IN RELATION TO THE LEVEL OF PROTEINS | | | | |
| --- | --- | --- | --- | --- |
| Products | Concentrations | O.D.—Blank collagen VII/ 100 μg proteins/72 h | p (test t) with respect to the control | Significance |
| Control SFMc 2% + DMSO 0.1% | — | 1.099 +/− 0.165 | | |
| AE | 2.5 μg/ml | 1.557 +/− 0.238 | 0.004 | S (+42%) |
| AE | 10 μg/ml | 1.490 +/− 0.204 | 0.004 | S (+36%) |

N.S.: non significant
S: significant (p < 0.05)

The results appearing in Table III show a significant stimulation of collagen VII by the aqueous extract of Potentilla erecta with concentrations of 2.5 and 10 μg/ml.

Thus, it appears clearly that the extracts of Potentilla erecta stimulate the formation of collagen VII. This protein notably being the main constituent of anchoring fibrils, these extracts can therefore advantageously be used as an agent for reinforcing the dermo-epidermal junction, and for thus improving the cohesion between the dermis and the epidermis.

Furthermore, it is known notably from the publication by M. Akiyama cited above, that collagen VII is indispensable for the expression of the mitotic activity of the keratinocytes of the human hair follicles, from where the interest comes of the extracts of Potentilla erecta for improving hair condition.

EXAMPLE 9

Demonstration of the Stimulation of the Synthesis of Collagen VII by a Methanol Extract of Rhizomes of Potentilla erecta This demonstration is carried out with a methanol extract, hereinafter designated as <<ME>>, obtained according to the method described in Example 6.

The experimental protocol used is exactly the same as that described in the preceding Example in relation to the test with the aqueous extract, except that the normal human keratinocytes (NHK) used this time originate from a lifting on a 56-year old Caucasian woman.

The results obtained are given in Table IV below, from the average of the measurements on the various cultures.

TABLE IV

COLLAGEN VII COMPARED TO THE LEVEL OF PROTEINS

| Products | Concentrations | O.D.—Blank collagen VII/ 100 µg proteins/72 h | p (test t) with respect to the control | Significance |
|---|---|---|---|---|
| Control SFMc 2% + DMSO 0.1% | — | 1.096 +/− 0.146 | | |
| ME | 1 µg/ml | 1.155 +/− 0.069 | 0.3987 | N.S. (+5%) |
| ME | 2.4 µg/ml | 1.387 +/− 0.186 | 0.0138 | S (+26%) |
| ME | 5 µg/ml | 1.422 +/− 0.199 | 0.0100 | S (+30%) |

N.S.: non significant
S: significant ($p < 0.05$)

The results appearing in Table IV above show that the methanol extracts according to the invention possess, from a certain concentration, a very significant effect of stimulation of the formation of collagen VII.

These results confirm the conclusions of the test relating to the aqueous extracts of the preceding Example, namely that the extracts of the plant Potentilla erecta have great importance firstly in the reinforcement of the cutaneous dermo-epidermal junction, and secondly, in the improvement of hair condition.

Extracts of *Bertholletia*.

In another preferred embodiment, the stimulant of collagen VII synthesis is an extract of *Bertholletia*, particularly *Bertholletia excelsa*.

In another embodiment, the extract of *Bertholletia* is an extract of the bark of this plant, particularly an extract of the trunk of the *Bertholletia excelsa* plant.

In another embodiment, the extract of *Bertholletia* is an extract of the fruits, i.e. the nuts, of *Bertholletia*, preferably extracts of the pericarp of the nuts of *Bertholletia*, and particularly preferably *Bertholletia excelsa*.

In particular, the extract of *Bertholletia* can be obtained by the process described below by way of indication, but without implying a limitation.

A first extraction is carried out on the bark or the nuts of the plant, particularly the bark of the trunk or the pericarp of the nuts, with a polar solvent advantageously selected from the group comprising water, alcohols preferably containing from 1 to 4 carbon atoms, chlorinated solvents preferably containing 1 or 2 carbon atoms, organic esters preferably containing from 3 to 6 carbon atoms, and a mixed solvent based on any mixture of the above-mentioned solvents.

Particularly preferably, the first extraction solvent is selected from the group consisting in water, methanol, ethanol, methanol/water mixtures, ethanol/water mixtures, chloroform and dichloromethane and their mixtures. Particularly preferably, the solvent is water, methanol, ethanol or any mixture of these solvents.

The ratio of the bark or the nuts, particularly the pericarp of the nuts, to the extraction agent is not critical and will generally be between 1:5 and 1:20 parts by weight.

The extraction is generally carried out at temperatures between room temperature and the boiling point of the solvent used for the extraction.

This first extraction is preferably carried out under reflux at atmospheric pressure for a period of 2 to 4 h. It is also advantageously preceded by a cold maceration for 2 to 4 h in the extraction solvent.

When extraction is complete, the solvent phase containing the extract is filtered and then concentrated and/or evaporated to dryness under reduced pressure to give a first crude extract of *Bertholletia* according to the invention. This crude extract can be purified by various processes well known to those skilled in the art.

The extracts of *Bertholletia*, more particularly *Bertholletia excelsa*, are rich in saponins. Also, these extracts, particularly the extracts of the pericarp of the nuts of *Bertholletia excelsa*, contain tannins, particularly ellagotannin and gallotannins, irrespective of the polar extraction solvent used, such as water or methanol.

In particular, if it is desired to enrich the extract of *Bertholletia* according to the invention in saponins, the process described below by way of indication, but without implying a limitation, is used. The extract obtained after the first extraction is evaporated to dryness. The residue is then taken up with methanol. The solution obtained is poured into acetone. The precipitate which then forms is recovered by filtration. Preferably, this precipitate is dried and then dialyzed against demineralized water. Finally, the product is lyophilized to give a dry extract of *Bertholletia* enriched in saponins, according to the invention.

The extraction processes described above apply in particular to the species *Bertholletia excelsa*.

The invention also covers a method of cosmetic or pharmaceutical treatment, especially dermatological treatment, characterized in that it comprises the application of an amount of an extract of *Bertholletia*, especially *Bertholletia excelsa*, particularly dispersed in a cosmetically or pharmaceutically acceptable excipient, said amount being cosmetically or pharmaceutically effective for a cosmetic or pharmaceutical treatment. Said application is preferably a topical application to areas of the skin in question. The cosmetic or pharmaceutical applications which are particularly advantageous at the present time result from the foregoing description and the following description relating to the Examples, and from the claims. The same applies to the extract concentration.

In one or other of the above features, the extract of *Bertholletia*, particularly *Bertholletia excelsa*, will preferably be used at a concentration of between 0.0001% and 1% by weight, based on the total weight of the final composition. This concentration is preferably between 0.01% and 0.25% by weight, based on the total weight of the final composition.

In the following Examples, the percentages are expressed by weight unless indicated otherwise. The amounts of the extracts are expressed by dry weight.

EXAMPLE 10

Preparation of a Methanolic Extract of the Bark of the Trunk of *Bertholletia Excelsa*, Enriched in Saponins Powdered bark of the trunk of *Bertholletia excelsa* is prepared by grinding. 49 g of this powder are then macerated for 2 h in 500 ml of methanol. The whole mixture is refluxed for 3 h and then left to cool and filtered on a glass frit. The filtrate obtained constitutes a first extract according to the invention, called extract $I_1$. This first extract is evaporated to dryness. The residue, weighing 14.7 g, is taken up with 100 ml of methanol. This solution is poured into 500 ml of acetone to give a precipitate, which is then filtered off. The precipitate is subsequently dried over a solid dehydrating agent, such as potassium hydroxide, to give 1.33 g of dry product. 830 mg of this product are subsequently dialyzed for 4 days against 9 ml of demineralized water and then lyophilized to give 182 mg of saponin-enriched extract according to the invention, called extract $I_2$.

EXAMPLE 11

Preparation of a Methanolic Extract of the Pericarp of Nuts of the Brazilian *Bertholletia excelsa*, Enriched in Saponin The pericarps of nuts of the Brazilian *Bertholletia excelsa*, which are commercially available, are collected and ground coarsely and finely.

100 g of the resulting powdered nut pericarp are then extracted three times in succession with 1 l of methanol under reflux for 30 min.

Each extract is filtered on a filter of pore diameter 0.45 µm and the three extracts are combined.

The combined extracts are concentrated on a rotary evaporator until a dry film is obtained.

This film is taken up by shaking with water. The resulting milk is lyophilized.

This gives about 5 g of saponin-enriched extract of nut pericarp according to the invention, called extract $I_3$. It will be noted that the yield of the extraction is of the order of 5%.

EXAMPLE 12

Demonstration of the Activity of a Methanolic Extract of the Bark of *Bertholletia excelsa*, Prepared According to Example 9, Extract $I_2$, on Collagen I Synthesis by Human Fibroblasts in Culture Culture of Fibroblasts Cultures of fibroblasts of healthy adult dermis are prepared by the explant method using a sample of facial skin obtained from a 60-year-old woman in the course of a face-lift.

The fibroblasts are cultivated to the point of confluence in an E 199 medium (Gibco) supplemented with 2 mmol/l of L-glutamine (Gibco) and 10% v/v of fetal calf serum (Gibco) at 37° C. in a humidified atmosphere containing 5% of $CO_2$. For evaluation of the collagen content, the primary cultures in confluence are harvested with a solution containing 0.1% of trypsin and 0.02% of EDTA in phosphate buffered saline (PBS) at pH 7.2 and the cells are then inoculated, at a density of $10^4$ fibroblasts per well, into 96-well microculture plates (Falcon) in the presence of the same culture medium as that described above.

24 h after inoculation, the medium is removed and replaced with a medium of the same composition as the medium described above, except that it does not contain serum and that 25 µmol/l of L-ascorbic acid in the form of the sodium salt have been added. Moreover, this new medium may or may not contain the test product (extract $I_2$), depending on whether it is a treated culture or a control culture. Incubation is then carried out for an additional period of 48 h at 37° C. The test product (extract $I_2$) has been dissolved in DMSO before incorporation into the culture medium (the final concentration of DMSO in the medium is 0.1% v/v).

Viability of the Cells

At the end of the incubation period, the medium is removed and an MTT cell viability test was performed according to the publication by Denizot F. et al., J. Immunol. Methods, (1986) 89, 271-277. The cells are incubated with 100 µl of a solution containing 0.5 mg/ml of tetrazolium salt (3-[4,5-dimethylthiazol-2-yl]-2,5-diphenyltetrazolium bromide or MTT) in E 199 medium without phenol red (Gibco) for 3 h at 37° C. 100 µl of isopropanol are then added to each well in order to solubilize the dark-colored formazan blue derivative formed by the living cells. The absorbance is measured at 540 nm.

Measurement of the Collagen

The total amount of type I collagen secreted by the fibroblasts, which is found either associated with the cells or released into the serum-impoverished medium after incubation for 48 h with or without the product (extract $I_2$), is determined by an ELISA test as previously described in the publication by Dumas M. et al., Mech. Ageing Dev. (1994) 73 179-187, and the publication by Grimaud J. P. et al., in: Methods of Enzymatic Analysis (Bermeyer, H. U., ed.), VCH Publishers, Weinheim, (1986), 186-201.

The serum-impoverished incubation media and the residual cells, homogenized by sonication in ice, are collected and transferred to the wells of a plastic immunotiter plate (NUNC) for a 24 h incubation at +4° C. to allow the secreted collagen to adhere. Protease inhibitors (ethylmaleimide, phenylmethylsulfonyl fluoride and ethylenediaminetetraacetate, each in a final concentration of 1 mM) are added during this period. The plates are then rinsed with PBS. A similar washing step is carried out after each plate treatment.

After incubation for 24 h at 4° C. with serum albumin to prevent non-specific binding, anti-human type I collagen rabbit antibodies (Institut Pasteur, Lyon, France) are added for 1.5 h at 22° C. and the bound antibodies are reacted with anti-rabbit goat IgG combined with alkaline phosphatase (Interchim, Montlucon, France). The absorbance of the paranitrophenol formed from paranitrophenyl phosphate (Sigma) by the alkaline phosphatase is measured at 405 nm. The optical densities are converted to nanograms of collagen using a calibration curve established with purified human type I collagen (Institut Jacques Boy, France).

Statistics

The amounts of collagen (mean.±.SD, standard deviation, n=6) are compared with those determined on the untreated control cultures. The significance of this comparison is assessed for values of p below 0.05 by the Student t test.

Results

The percentage stimulation A of collagen I synthesis is calculated by comparing the amounts of collagen I secreted in the control cultures (without any test product), $C_o$, and in the treated cultures, $C_t$, on the basis of the following formula:

$$A = \frac{C_t - C_O}{C_O} \times 100$$

The results are collated in Table V below.

TABLE V

| Culture | % viability/ control | Collagen I secreted by fibroblasts (ng/10,000 cells/48 h) | % stimulation A | Significance |
|---|---|---|---|---|
| Control culture without product | 100 | 924 | 0 | |
| Product of the invention $I_2$ at 1 µg/ml | 100 | 1359 | +47 | S* |

TABLE V-continued

| Culture | % viability/ control | Collagen I secreted by fibroblasts (ng/10,000 cells/48 h) | % stimulation A | Significance |
|---|---|---|---|---|
| Product of the invention $I_2$ at 2.5 µg/ml | 100 | 2163 | +134 | S* |

*S = significant

An examination of Table V shows first of all that the percentage viability of the cells in the treated cultures has not varied significantly compared with that of the control cultures. The extract $I_2$ therefore exhibits no cytotoxicity.

In this Table the amounts of collagen I secreted by the fibroblasts have been expressed in ng/10,000 cells/48 h.

It will be observed from Table V that the methanolic extract of Bertholletia excelsa has produced a significant stimulating activity on collagen I synthesis by the fibroblasts.

Thus the extract of *Bertholletia excelsa* can be used for products which are intended for combating skin ageing or which require an increase in local collagen synthesis, as is the case of a wrinkle treatment, or for contributing to an improvement in skin healing.

EXAMPLE 13

Demonstration of the Activity of a Methanolic Extract of the Pericarp of Nuts of Bertholletia excelsa According to the Invention, Extract $I_3$, on Collagen IV Synthesis by Human Keratinocytes in Culture Culture of the Keratinocytes Human keratinocytes originating from a face-lift on a 60-year-old woman with caucasian skin are cultivated in a Gibco keratinocyte-specific growth medium, SFM-K, complemented with EGF (epidermal growth factor) and pituitary extract (Gibco, France). The cells are inoculated into this SFM-K medium at a rate of 30,000 per culture well.

After 24 h the inoculation medium is withdrawn and replaced with SFM-K medium diluted to 1/50 in the same base medium but without EGF and pituitary extract. The test product (dissolved in DMSO) will then be added at the different concentrations for 48 h. The control cultures will receive the same amount of solvent for the test product, in this case DMSO (final concentration 0.1%).

The culture supernatants are recovered and the collagen IV is assayed by a conventional ELISA technique previously described in Dumas M. et al., Mechanisms of Ageing and Development, 73, 1994, pages 179-187. The anti-human collagen IV antibody used is supplied by the Institut Pasteur, Lyon, France.

At the same time an overall assay of the proteins is performed by the bicinchoninic acid technique using a BCA kit marketed by Sigma, France.

The results obtained are reported in Table VI below:

TABLE VI

| PRODUCT | Collagen IV ng/100 µg of proteins | Percentage activity | Significance |
|---|---|---|---|
| DMSO control | 1.499 ± 0.635 | | |
| Product of the invention $I_3$ at 1 µg/ml | 2.983 ± 0.613 | +99 | S* |
| Product of the invention $I_3$ at 10 µg/ml | 3.153 ± 0.732 | +110 | S* |

*S = significant at the 5% level

An examination of Table VI shows very clearly that the test extract significantly stimulates collagen IV synthesis by the human keratinocytes in culture. One of its applications is therefore to strengthen the structure and properties of the epidermal-dermal junction, an exchange zone between the dermis and the epidermis and a very important zone for the keratinocyte differentiation processes.

EXAMPLE 14

Demonstration of the Stimulation of Collagen VII Synthesis

The following test was performed on the extract $I_3$ recovered in Example 11.

The tests were performed blind.

1—Test Protocol a) Origin of the Keratinocytes

The cultures of normal human keratinocytes (NHK) are prepared from a surgically removed sample of healthy skin. In the present study, the tests were performed on a cellular strain originating from a face-lift carried out on a 44-year-old caucasian woman (strain denoted by HK 44 years). The results were confirmed on another cellular strain, denoted by HK 56 years, originating from a face-lift carried out on a 56-year-old caucasian woman.

b) Culture Conditions

The keratinocytes are kept in complete serum free medium (denoted by SFMc, GIBCO). The cells were subcultivated once from the primary culture (i.e. one pass, denoted by P1).

c) Treatment Conditions

The cells are inoculated into SFMc in a 96-well culture dish at a rate of 30,000 NHK per well. After incubation for 24 h, which is necessary for good adhesion of the cells, the medium is replaced with SFMc diluted to 2%, limiting the proliferation of the keratinocytes. The stock solutions of the product obtained according to Example 13 (denoted by $I_3$ in Table VI) are prepared immediately before use in DMSO at concentrations of 1, 2.5 and 5 mg/ml and are introduced into the test medium at a final concentration of 0.1% v/v (i.e. the test concentrations are 1, 2.5 and 5 µg/ml). The control receives the excipient for the product, i.e. 0.1% v/v of DMSO. Neither the XTT viability test nor microscopic observation of the cells revealed cytotoxic effects of the product at concentrations below 10 µg/ml (BOEHRINGER XTT kit, ref. 1465015).

The cells are brought into contact with the treatment medium for 72 h, which is the time required for optimum collagen VII synthesis according to a prior kinetics study.

The incubation supernatants are removed for assay of the collagen VII secreted. The proteins are assayed on the cellular mat remaining in the wells (BCA method, SIGMA) for the purpose of determining the ratio of the amounts of collagen VII secreted to the amounts of cellular proteins.

Six cultures are prepared for each of the three concentrations and for the control experiment.

d) ELISA Assay of the Collagen VII

The protocol for assaying the collagen VII by an ELISA method was adapted from that used for assaying collagen I (M. DUMAS, C. CHAUDAGNE, F. BONTE, A. MEYBECK: "In vitro biosynthesis of type I and III collagens by human dermal fibroblasts from donors of increasing age". Mechanisms of Ageing and Development, 73 (1994) 179-187).

The following modifications were made:

1st antibody: Anti-human type VII collagen monoclonal mouse antibody, isotype IgG1 (Life Technologies, ref. 12073-011).

2nd antibody: Anti-total mouse IgG goat antibody coupled with alkaline phosphatase (Interchim, ref. 115-056-062).

e) Expression of the Results and Statistical Interpretation

In the absence of commercially available human type VII collagen to establish a calibration range, the results of collagen VII secretion by the keratinocytes are expressed in optical density units, from which the control extract of the assay is subtracted (denoted by OD—blank). These values are adjusted for the amount of cellular proteins in the corresponding well (for 72 h of incubation).

The activity of the product is evaluated by the percentage stimulation: [(collagen VII in treated NHK—collagen VII in control NHK)/collagen VII in control NHK] X100.

The results obtained on the treated and control cultures are compared by the unpaired Student test, the chosen significance level being p<0.05.

Results—Conclusion

The results are given in Table VII below on the basis of the mean of the measurements on the different cultures:

TABLE VII

| Product | Cellular viability without HX/XO | Cellular viability with HX/XO | Significance |
|---|---|---|---|
| Control | 100% | 40% | |
| Extract $I_3$ of the invention at 1.25 µg/ml | 100% | 56% | S* |
| Extract $I_3$ of the invention at 5 µg/ml | 100% | 81% | S* |

*S = significant at the 5% level

These results clearly show that the extract of *Bertholletia excelsa* $I_3$ very strongly stimulates the synthesis of collagen VII, the main constituent of the anchoring fibrils. Thus extracts of *Bertholletia* can therefore advantageously be used in cosmetic or dermatological compositions or cell culture media for improving the epidermal-dermal junction.

The invention claimed is:

1. A cosmetic composition comprising magnesium aspartate, in an effective amount for promoting the adhesion of the keratinocytes of the epidermal basal layer to the dermo-epidermal junction, in association with at least one collagen stimulating active agent for stimulating synthesis of collagen IV or of collagen VII, said agent for stimulating collagen IV being selected from the group consisting of soya saponins, soya sapogenols and plant extracts rich in soya saponins or soya sapogenols or comprising saponins from roots of *Medicago sativa* and said agent for stimulating the synthesis of collagen VII being selected from the group consisting of an extract of *Potentilla erecta* and an extract of *Bertholletia*.

2. The composition of claim 1, wherein said agent stimulating the synthesis of collagen IV is selected from the group consisting of soya saponins, or soya sapogenols.

3. The composition of claim 1, wherein said active agent for stimulating the synthesis of collagen VII is an extract of Bertholletia.

4. The composition according to claim 1, comprising 0.3 g of magnesium aspartate and 0.01 g of a dried extract of Potentilla erecta per 100 g of said composition.

5. The composition according to claim 1, which comprises 0.3 g of magnesium aspartate and 1 g of a dried extract of Potentilla erecta per 100 g of said composition.

6. The composition of claim 1, comprising between, 0.001 and 5% by weight of said magnesium aspartate based on the total weight of the composition.

7. The composition of claim 1, wherein said agent stimulating the synthesis of collagen IV is selected from the group consisting of soya saponins, soya sapogenols, and plant extracts rich in soya saponins or soya sapogenols.

8. The composition of claim 1, wherein said agent stimulating the synthesis of collagen IV comprises saponins from roots of *Medicago sativa*.

9. The composition of claim 1, wherein said active agent stimulating the synthesis of collagen VII is an extract of *Potentilla erecta*.

10. The composition of claim 1, comprising between 0.001 and 1% by weight of said magnesium aspartate based on the total weight of the composition.

11. The composition of claim 1, further comprising a magnesium complex with a $C_2$-$C_{12}$ aliphatic alpha-hydroxy acid selected from the group consisting of citric acid, glycolic acid, gluconic acid, malic acid, lactic acid, and 2-hydroxybutyric acid, and mixtures thereof, in an effective amount for promoting the adhesion of the keratinocytes of the epidermal basal layer to the dermo-epidermal junction.

* * * * *